US012690969B2

(12) United States Patent
Smith et al.

(10) Patent No.: US 12,690,969 B2
(45) Date of Patent: Jul. 28, 2026

(54) INFLATABLE PROSTHESIS HAVING A PRESSURE CALIBRATION SYSTEM

(71) Applicant: Boston Scientific Scimed, Inc., Maple Grove, MN (US)

(72) Inventors: Noel Smith, Windgap (IE); John Gildea, Kilcock (IE); Brian P. Watschke, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1109 days.

(21) Appl. No.: 17/653,232

(22) Filed: Mar. 2, 2022

(65) Prior Publication Data

US 2022/0280299 A1     Sep. 8, 2022

Related U.S. Application Data

(60) Provisional application No. 63/200,371, filed on Mar. 3, 2021.

(51) Int. Cl.
*A61F 2/26* (2006.01)

(52) U.S. Cl.
CPC ........ *A61F 2/26* (2013.01); *A61F 2250/0003* (2013.01); *A61F 2250/0013* (2013.01); *A61F 2250/0058* (2013.01)

(58) Field of Classification Search
CPC ..................................... A61F 2/26; A61F 5/41
See application file for complete search history.

(56) References Cited

U.S. PATENT DOCUMENTS

| | | | | |
|---|---|---|---|---|
| 4,941,461 | A | * | 7/1990 | Fischell .................... A61F 2/26 |
| | | | | 52/2.21 |
| 2004/0024324 | A1 | | 2/2004 | Bratteli |
| 2012/0022324 | A1 | | 1/2012 | Forsell |
| 2016/0030178 | A1 | * | 2/2016 | Forsell ...................... A61F 2/26 |
| | | | | 600/40 |
| 2016/0206429 | A1 | | 7/2016 | Forsell |
| 2017/0325960 | A1 | * | 11/2017 | Forsell ................. A61B 5/4393 |

(Continued)

FOREIGN PATENT DOCUMENTS

| | | |
|---|---|---|
| AU | 2019269370 B2 | 11/2021 |
| CN | 1416329 A | 5/2003 |

(Continued)

OTHER PUBLICATIONS

Invitation to Pay Additional Fees for PCT Application No. PCT/US2022/070942, mailed on Jun. 9, 2022, 10 pages.

(Continued)

*Primary Examiner* — Charles A Marmor, II
(74) *Attorney, Agent, or Firm* — Brake Hughes Bellermann LLP

(57) ABSTRACT

According to an aspect, an apparatus includes a bodily implant configured to be implanted into a body of a patient. The implant having an inflatable member, a sensor, and a calibration module. The inflatable member is configured to be disposed within a portion of the body of the patient. The sensor is operatively coupled to the inflatable member and is configured to detect a fluidic pressure within the inflatable member. The calibration module is configured to receive pressure data from the sensor and determine when the inflatable member is sufficiently inflated.

18 Claims, 7 Drawing Sheets

(56) References Cited

U.S. PATENT DOCUMENTS

2018/0110623 A1*  4/2018  Vaingast  .................. A61F 2/26
2019/0350712 A1    11/2019  Weber et al.

FOREIGN PATENT DOCUMENTS

WO      2009094431 A2    7/2009
WO      2014152968 A1    9/2014
WO      2015200784 A3    12/2015

OTHER PUBLICATIONS

First Examination Report for Australian Application No. 2025203172, dated Apr. 23, 2026, 3 pages.
First Office Action for Chinese Application No. 202280018842.2 (with English translation), dated May 8, 2026, 16 pages.

* cited by examiner

100

110

130

120

INFLATABLE PROSTHESIS HAVING A PRESSURE CALIBRATION SYSTEM

CROSS-REFERENCE TO RELATED APPLICATION

This application claims priority to U.S. Provisional Patent Application No. 63/200,371, filed on Mar. 3, 2021, entitled "INFLATABLE PROSTHESIS HAVING A PRESSURE CALIBRATION SYSTEM", the disclosure of which is incorporated by reference herein in its entirety.

TECHNICAL FIELD

This disclosure relates generally to a medical device having an inflatable member and a pressure calibration system.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism transfers fluid between a fluid reservoir and the inflatable members to inflate and deflate the inflatable members. In some cases, it can be important to not overinflate or over deflate the inflatable member so as to conserve battery power and/or have an otherwise efficient system. Additionally, it can be important to not fully deflate the inflatable member so as to help retain a normal shape when in the deflated state.

Accordingly, there is a need for a medical device that may be inflated within the body of the patient and includes a calibration system.

SUMMARY

According to an aspect, an apparatus includes a bodily implant configured to be implanted into a body of a patient. The implant having an inflatable member, a sensor, and a calibration module. The inflatable member is configured to be disposed within a portion of the body of the patient. The sensor is operatively coupled to the inflatable member and is configured to detect a fluidic pressure within the inflatable member. The calibration module is configured to receive pressure data from the sensor and determine when the inflatable member is sufficiently inflated.

In some embodiments, the inflatable member is configured to be disposed in an inflated configuration and a deflated configuration. In some embodiments, the inflatable member is configured to be disposed in an inflated configuration and a deflated configuration, the inflatable member being configured to have a first rigidity when the inflatable member is in its inflated configuration and a second rigidity when the inflatable member is in its deflated configuration. In some embodiments, the inflatable member is configured to be disposed in an inflated configuration and a deflated configuration, the inflatable member being configured to have a first rigidity when the inflatable member is in its inflated configuration and a second rigidity when the inflatable member is in its deflated configuration, the first rigidity being greater than the second rigidity.

In some embodiments, the bodily implant includes a pump, the pump being operatively coupled to the inflatable member and configured to pump a fluid out of the inflatable member. In some embodiments, the bodily implant includes a pump, the pump being operatively coupled to the inflatable member and configured to pump a fluid into the inflatable member. In some embodiments, the bodily implant includes a first pump and second pump. In some embodiments, the bodily implant includes an electric pump. In some embodiments, the bodily implant includes a first electric pump and a second electric pump.

In some embodiments, the bodily implant includes a reservoir configured to hold fluid.

In some embodiments, the calibration module includes an evaluation module, the evaluation module being configured to evaluate pressure data. In some embodiments, the calibration module includes a smoothing module, the smoothing module being configured to smooth pressure data received from the sensor.

In some embodiments, the inflatable member is configured to be disposed within a penis of the patient. In some embodiments, the inflatable member is configured to be disposed in a linear configuration. In some embodiments, the inflatable member is configured to be disposed in a linear configuration and is configured be disposed within a penis of the patient.

According to another aspect an apparatus includes a bodily implant configured to be implanted into a body of a patient, the implant including an inflatable member, a reservoir, a first electrical pump, a second electrical pump, a sensor, and a calibration module, the inflatable member being configured to be disposed within a portion of the body of the patient, the first electrical pump being configured to pump fluid from the inflatable member to the reservoir, the second electrical pump being configured to pump fluid from the reservoir to the inflatable member, the sensor is operatively coupled to the inflatable member and is configured to detect a fluidic pressure within the inflatable member, and the calibration module is configured to receive pressure data from the sensor and determine when the inflatable member is sufficiently rigid.

In some embodiments, the inflatable member is configured to be disposed within a penis of the patient.

In some embodiments, the inflatable member is configured to be disposed in a linear configuration and is configured to be disposed within a penis of the patient.

According to another aspect, a method includes inflating an inflatable member that is disposed within a body of a patient; sensing the pressure within the inflatable; and determining when the inflatable member is sufficiently rigid.

In some embodiments, the method includes smoothing pressure data received from a pressure sensor.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The bodily implant disclosed herein are configured to be disposed within a body of a patient. In some embodiments, the bodily implant includes an inflatable member or inflation member. In some embodiments, the inflatable member is configured to be inflated to expand a portion of the body of the patient. In some embodiments, the bodily implant may be placed within a pelvic region of a patient. In some embodiments, the bodily implant is a penile implant. In other embodiments, the implant may be another type of implant. In other embodiments, the bodily implant is configured to be placed in a different region of the body of the patient and is configured to expand or place pressure on a different portion of the body of the patient.

Figure 1:
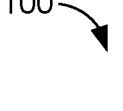
FIG. 1 schematically illustrates an apparatus according to an embodiment of the invention.
Figure 1:
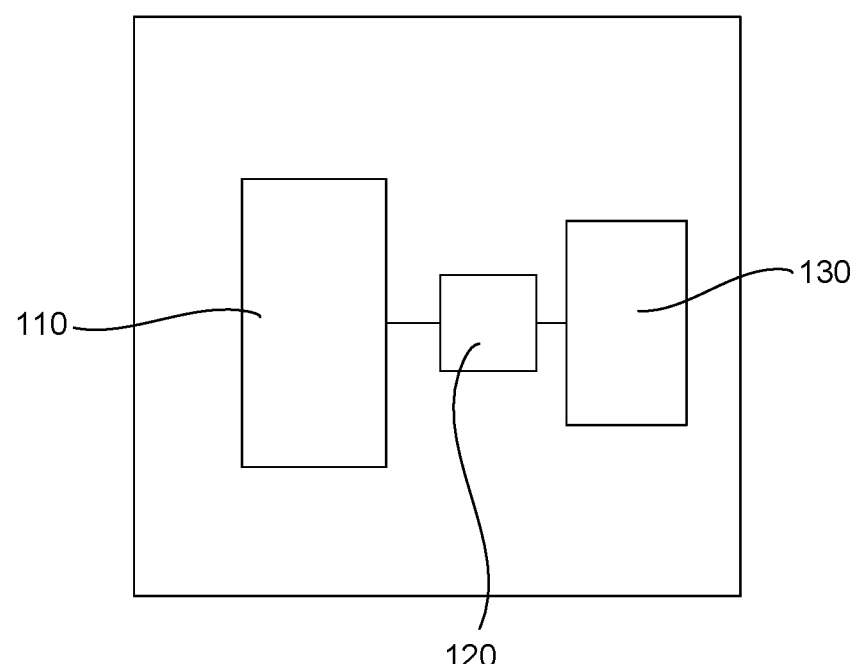

FIG. 1 illustrates an apparatus 100 according to an embodiment of the invention. In the illustrated embodiment, the apparatus or a bodily implant 100. The bodily implant 100 is configured to be disposed or otherwise placed within a body of a patient. In some embodiments, the bodily implant is configured to be placed within a pelvic region of a patient. For example, in some embodiments, the bodily implant is a penile implant configured to help address erectile dysfunction of the patient.

In the illustrated embodiment, the bodily implant 100 includes an inflatable or inflation member 110, a sensor 120, and a calibration module 130. The inflatable member 110 is configured to be placed in an inflated configuration and a deflated configuration. In some embodiments, the inflatable member 110 is configured to expand or enlarge to help expand or enlarge a portion of the body of the patient when the inflatable member 110 is in its inflated configuration. For example, in some embodiments, the inflatable member 110 is configured to be disposed within a penis of the patient and is configured to help address erectile dysfunction of the patient. In such an embodiment, the inflatable member 110 expands or enlarges to expand or enlarge the penis of the patient when the inflatable member 110 is in its inflated configuration and is in a smaller state does not expand or enlarge the penis of the patient (or expand or enlarges the penis of the patient less) when the inflatable member 110 is in its deflated configuration.

In some embodiments, the inflatable member 110 is formed of a material that is configured to expand. In some embodiments, the inflatable member 110 is a balloon or other inflatable type device. In some embodiments, the inflatable member 110 is or forms a tubular or cylindrical member.

The sensor 120 is operatively coupled to the inflatable member 110. The sensor 120 is configured to sense or detect a pressure within the inflatable member 110.

The calibration module 130 is operatively coupled to the sensor 120. The calibration module 130 is configured to receive pressure data of the inflatable member 110 from the sensor 120. In some embodiments, the calibration module 130 is configured to determine when the inflatable member 110 is applying pressure to the body of the patient. In some embodiments, the calibration module 130 is configured to determine when the inflatable member 110 is not applying pressure to the body of the patient. In some embodiments, the calibration module 130 is configured to determine when the inflatable member 110 is applying pressure to the body of the patient and when it is not applying pressure to the body of the patient.

In some embodiments, the calibration module 130 is configured to determine the atmospheric pressure of the location of the patient. For example, the calibration module 130 is configured to determine if the local atmospheric pressure is greater than normal (patient is diving in the ocean) or if the local atmospheric pressure is less than normal (patient is hiking a tall mountain).

Figure 2C:
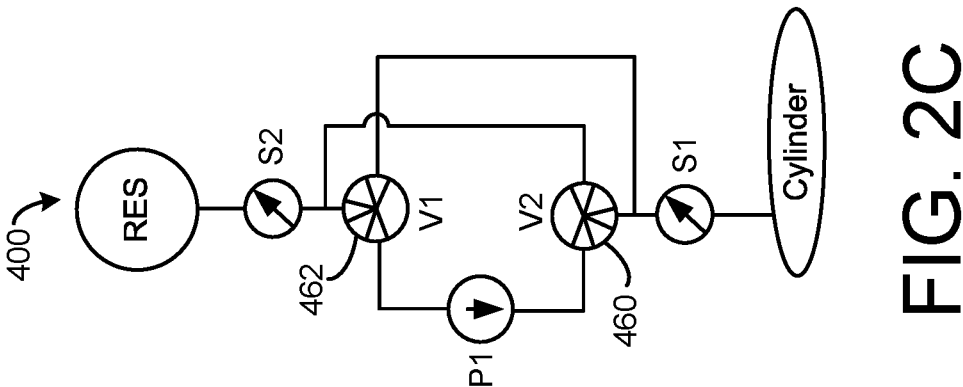
FIG. 2A-2C schematically illustrates apparatus according to other embodiments.
Figure 2B:
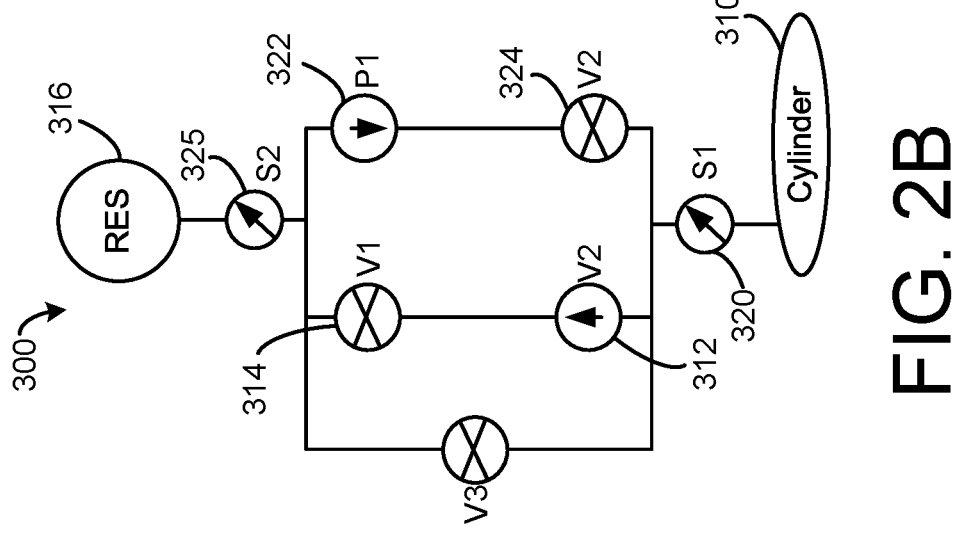
Figure 2A:
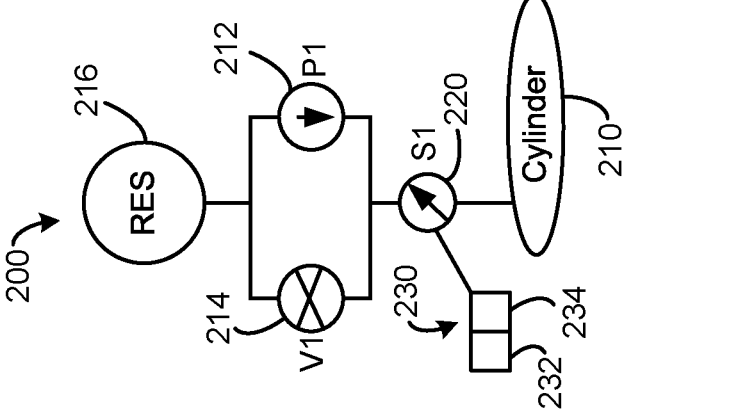

FIG. 2A schematically illustrates a bodily implant 200 according to an embodiment. The bodily implant 200 is configured to be disposed within a body of a patient. In the illustrated embodiment, the bodily implant 200 includes an inflatable or inflation member 210. The inflatable member 210 is configured to be placed in an inflated configuration and a deflated configuration. In some embodiments, the inflatable member 210 is configured to enlarge or expand a portion of the body of the patient when the inflatable member 210 is in its inflated configuration. In the illustrated embodiment, the inflatable member 210 is a cylinder that is configured to be placed within a penis of a patient. The inflatable member 210 increases in size and rigidity and thus increases the size or rigidity of the penis when the inflatable member 210 is in its inflated configuration and is smaller in size and rigidity when the inflatable member 210 is in is deflated configuration.

In some embodiments, the inflatable member 210 is formed of a material that is configured to expand. In some embodiments, the inflatable member 210 is a balloon or other inflatable type device.

The bodily implant 200 includes a pump 212, a valve 214 and a reservoir 216. The inflatable member 210 is operatively coupled to the pump 212. The reservoir 216 is also operatively coupled to the pump 212. For example, tubular members, such as kink-resistant tubular members, may be coupled to and extend from the inflatable member 210 to the pump 212 and from the reservoir 216 to the pump 212. The pump 212 is configured to pump fluid out of the reservoir 216. In the illustrated embodiment, the pump 212 is configured to pump fluid out of the reservoir 216 and towards or into the inflatable member 210. In some embodiments, the pump 212 is an electric pump or a pump that operates on an electrical power source.

The pump 212 is operatively coupled to the valve 214. For example, a tubular member, such as a kink-resistant tubular member, may be coupled to and extend from the pump 212 to the valve 214. The valve 214 is configured to control the flow of fluid between the reservoir 216 and the inflatable member 210.

The reservoir 216 is configured to hold fluid. In some embodiments, the reservoir 216 may be a pressure-regulating inflation balloon or element. The reservoir 216 may be constructed of polymer material that is capable of elastic deformation to reduce fluid volume within the fluid reservoir 216 and push fluid out of the fluid reservoir 216. In some embodiments, the reservoir 216 is made from an elastic material and is configured to expand when fluid is disposed in the reservoir 216. In some examples, the fluid reservoir 216 is implanted into the abdominal space. In other embodiments, the reservoir 216 is not a pressure-regulating member.

The bodily implant 200 also includes a sensor 220. The sensor 220 is operatively coupled to the inflatable member 210 and is configured to sense or detect the fluidic pressure within the inflatable member 210.

The bodily implant 200 also includes a calibration module 230. The calibration module 230 is operatively coupled to the sensor 220. The calibration module 230 is configured to receive pressure data of the inflatable member 210 from the sensor 220. In some embodiments, the calibration module 230 is configured to determine when the inflatable member 210 is in a sufficiently deflated state. In some embodiments, the calibration module 230 is configured to determine when the inflatable member 210 is in a sufficiently inflated state.

In some embodiments, the calibration module 230 is configured to determine the atmospheric pressure of the location of the patient. For example, the calibration module 230 is configured to determine if the local atmospheric pressure is greater than normal (patient is diving in the ocean) or if the local atmospheric pressure is less than normal (patient is hiking a tall mountain).

Figure 3:
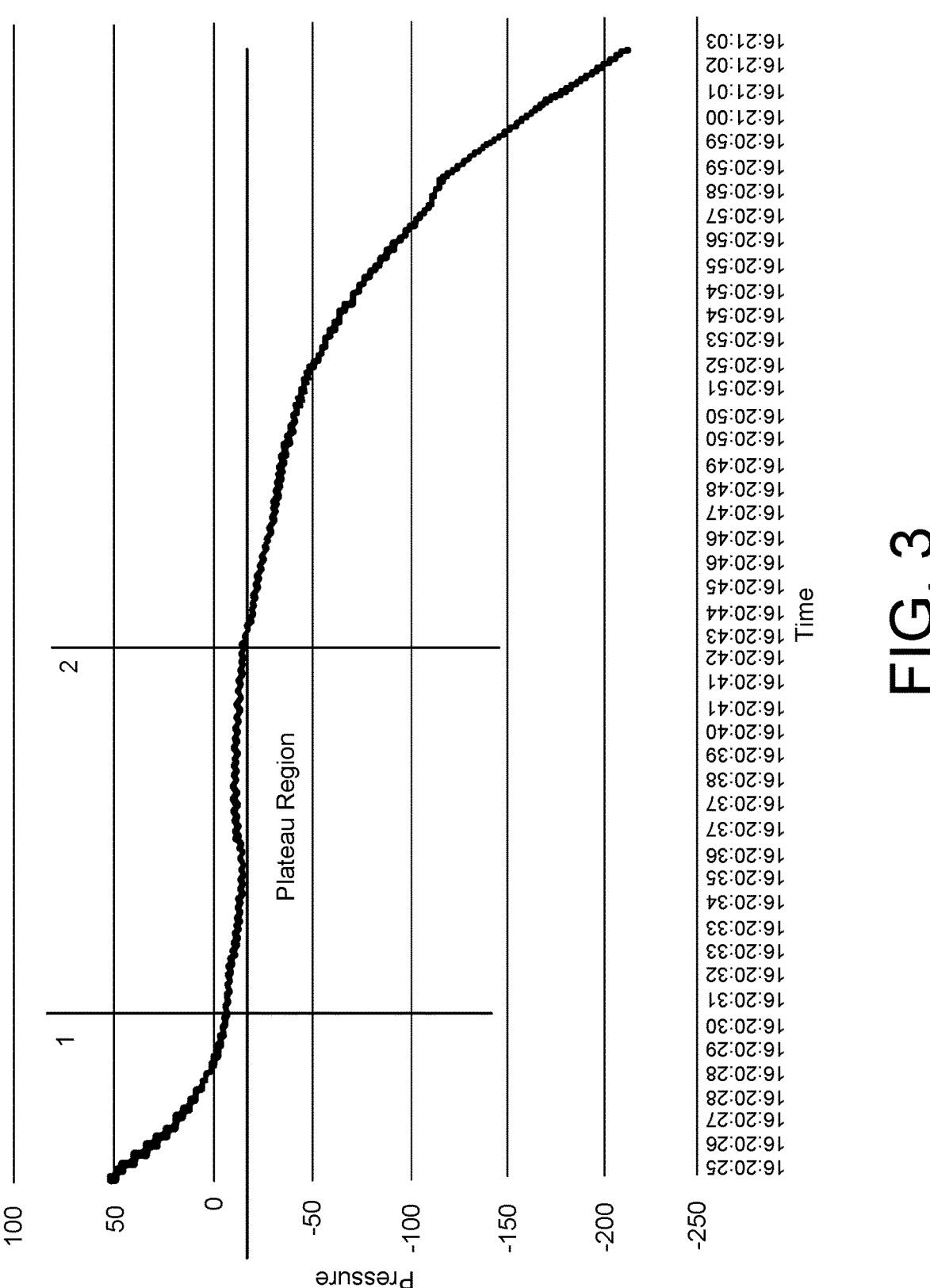
FIGS. 3-6 are graphs illustrating pressure over time of an apparatus according to an embodiment.

As best illustrated in FIG. 3, the pressure within the inflatable member 210 levels out for a period of time (the plateau region). In this region, the inflatable member 210 is no longer expanding or applying pressure to the portion of the body of the patient. Accordingly, the calibration module 230 can determine when the pump 212 can cease pumping fluid from the inflatable member 210. Specifically, in some embodiment, the pump 212 can cease pumping fluid from the inflatable member 210 at the beginning of the plateau region so as to conserve power resources.

In the illustrated embodiment, the calibration module 230 includes an evaluation module 232 and a smoothing module 234. The evaluation module 232 is configured to receive and evaluate pressure data received from the sensor 220. The smoothing module 234 is configured to smooth the pressure date received from the sensor 220.

Figure 4:
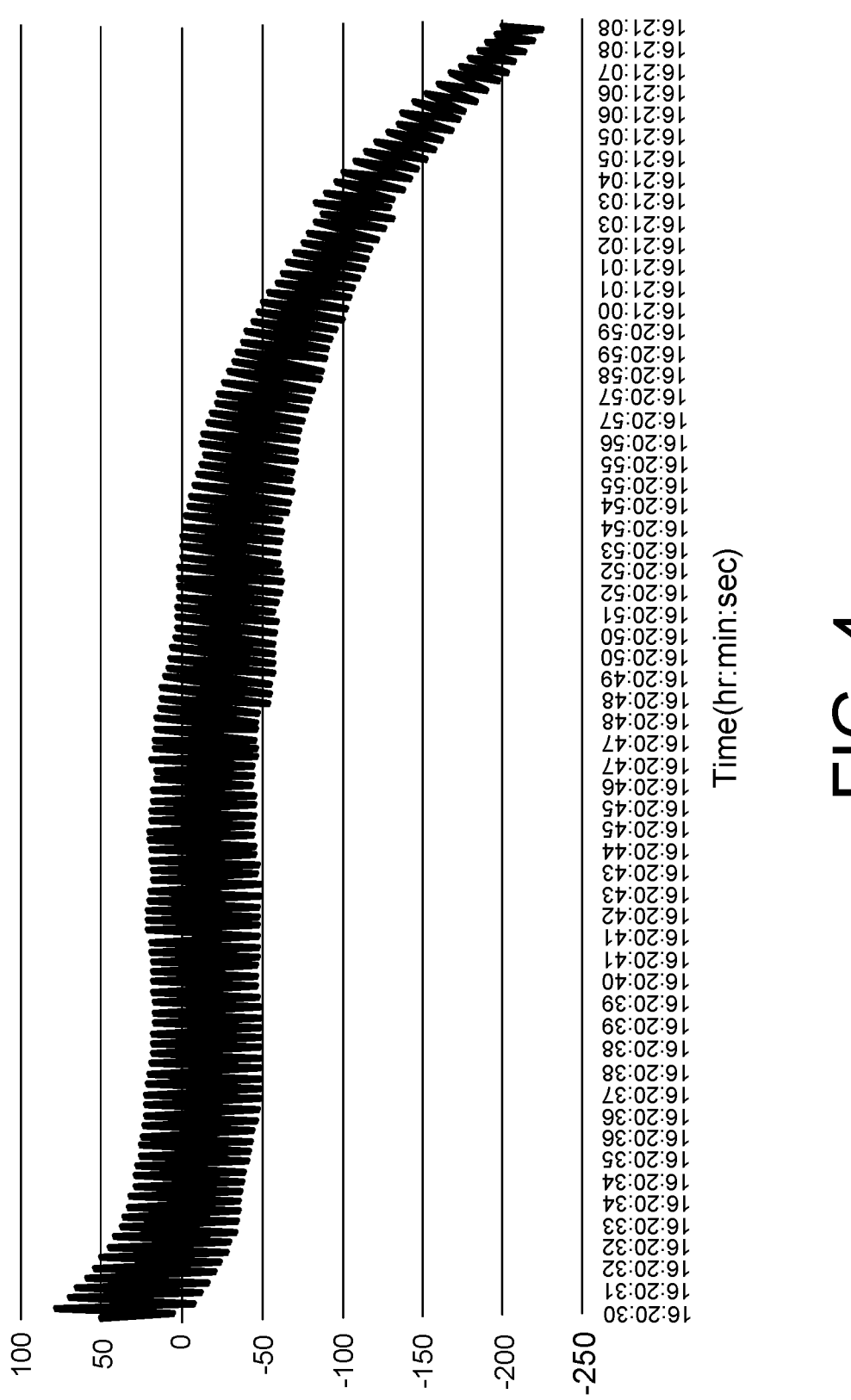
Figure 5:
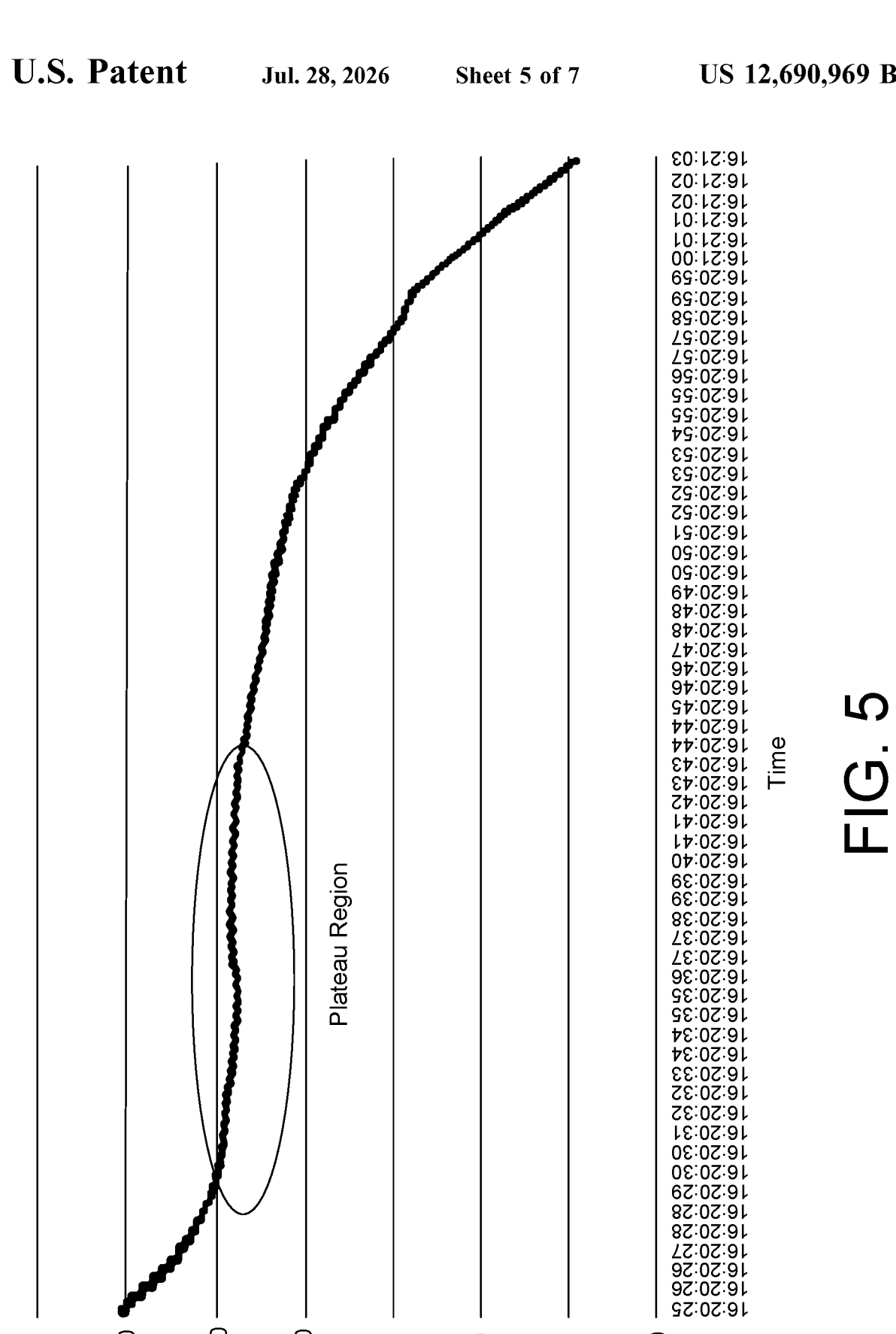
Figure 6:
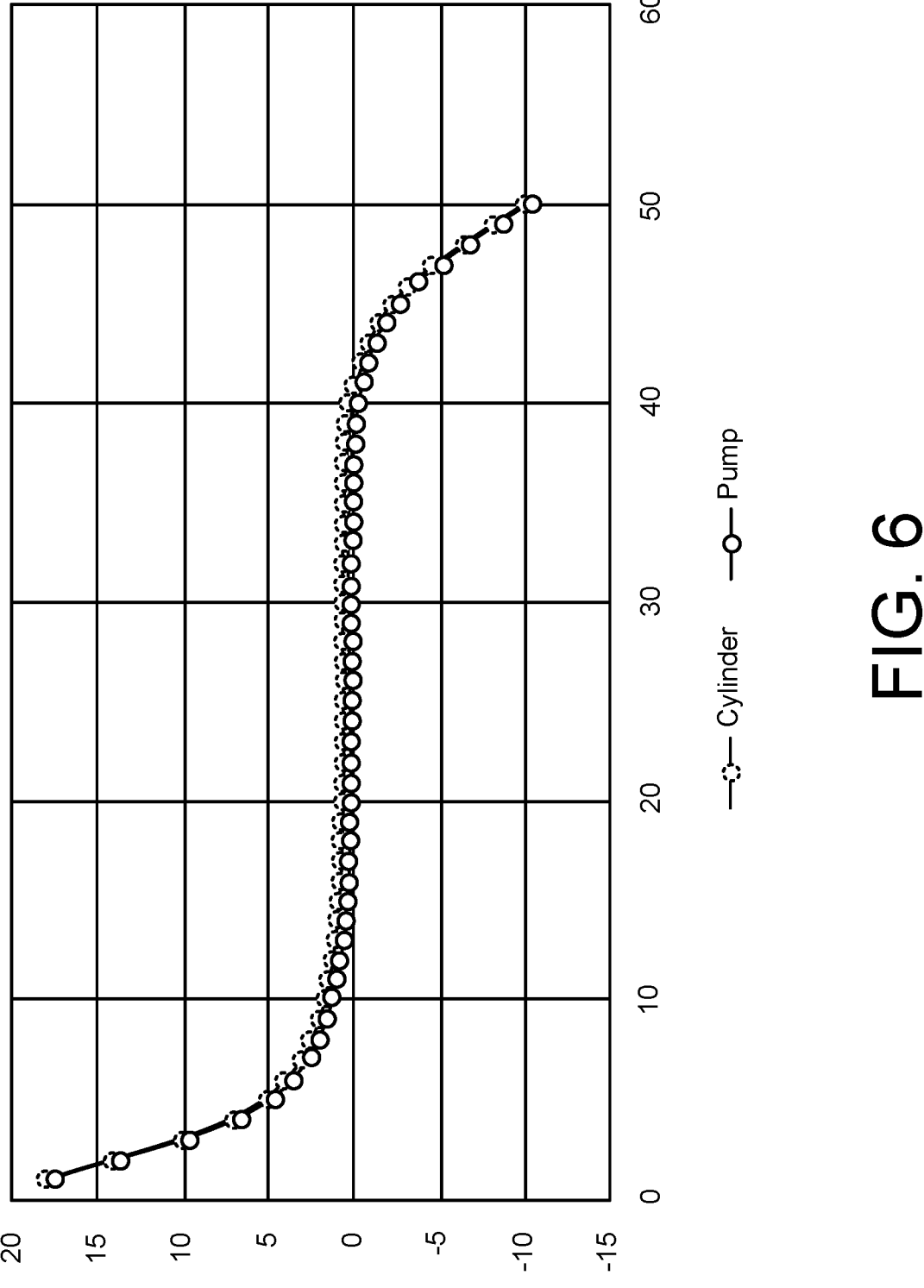

As best illustrated in FIG. 4, in some embodiments, the pressure data received from the sensor 220 oscillates. In some cases, the oscillation may make the plateau region difficult to identify. Accordingly, as illustrated in FIG. 5, the oscillating data may be smoothed to more easily and more accurately identify the plateau region. FIG. 6 also illustrates pressure data over time.

The smoothing module 234 may use any number of methods for smoothing the oscillating data. For example, in some embodiments, the smoothing module uses a standard deviation method to smooth the data. In this embodiment, the standard deviation of a subset of the data points will be the smallest at the plateau region. In another embodiment, the smoothing module uses a subtraction method to generate a smoothed curve. In such an embodiment, the value of the previous point is subtracted from the value of the current point to smooth the curve. In yet another embodiment, the inflection point or points of the oscillating curve may be identified to identify the plateau region.

FIG. 2B schematically illustrates a bodily implant 300 according to an embodiment. The bodily implant 300 includes a first pump 312, a first valve 314 and a reservoir 316. The inflatable member 310 is operatively coupled to the first pump 312. For example, a tubular member, such as a kink-resistant tubular member, may be coupled to and extend from the inflatable member 310 to the first pump 312. The first pump 312 is configured to pump fluid out of the inflatable member 310. In the illustrated embodiment, the first pump 312 is configured to pump fluid out of the inflatable member 310 and towards or into the reservoir 316. In some embodiments, the first pump 312 is an electric pump or a pump that operates on an electrical power source.

The first pump 312 is operatively coupled to the first valve 314. For example, a tubular member, such as a kink-resistant tubular member, may be coupled to and extend from the first pump 312 to the first valve 314. The first valve 314 is configured to allow fluid to pass in the direction towards the reservoir 316.

The first valve 314 is operatively coupled to the reservoir 316. A tubular member, such as a kink-resistant tubular member, extends between and couples the first valve 314 to the reservoir.

The reservoir 316 is configured to hold fluid. In some embodiments, the reservoir 316 may be a pressure-regulating inflation balloon or element. The reservoir 316 may be constructed of polymer material that is capable of elastic deformation to reduce fluid volume within the fluid reservoir 316 and push fluid out of the fluid reservoir 316. In some embodiments, the reservoir 316 is made from an elastic material and is configured to expand when fluid is disposed in the reservoir 316. In some examples, the fluid reservoir 316 is implanted into the abdominal space. In other embodiments, the reservoir 216 is not a pressure-regulating member.

The bodily implant 300 also includes a second pump 322 and a second valve 324. The reservoir 316 is operatively coupled to the second pump 322. For example, a tubular member, such as a kink-resistant tubular member, may be coupled to and extend from the reservoir 316 to the second pump 322. The second pump 322 is configured to pump fluid into the inflatable member 310. In the illustrated embodiment, the second pump 322 is configured to pump fluid out of the reservoir 316 and towards or into the inflatable member 310. In some embodiments, the second pump 322 is an electric pump or a pump that operates on an electrical power source.

The second pump 322 is operatively coupled to the second valve 324. For example, a tubular member, such as a kink-resistant tubular member, may be coupled to and extend from the second pump 322 to the second valve 324. The second valve 324 is configured to allow fluid to pass in the direction towards the inflatable member 310.

The second valve 324 is operatively coupled to the inflatable member 310. A tubular member, such as a kink-resistant tubular member, extends between and couples the second valve 324 to the inflatable member 310.

The bodily implant 300 also includes a first sensor 320 and a second sensor 325. The first sensor 320 is operatively coupled to the inflatable member 310 and is configured to sense or detect the fluidic pressure within the inflatable member 310. The second sensor 325 is operatively coupled to the reservoir 316 and is configured to sense or detect the fluidic pressure within the reservoir 316.

The bodily implant 300 also includes a calibration module as described above with respect to the implant 200.

FIG. 2C schematically illustrates a bodily implant 400 according to an embodiment. The bodily implant 400 includes a pair of three-way valves 460 and 462 to help facilitate the inflation and deflation of the inflatable member.

Figure 7:
FIG. 7 is a flow chart of a method according to an embodiment.
Figure 7:
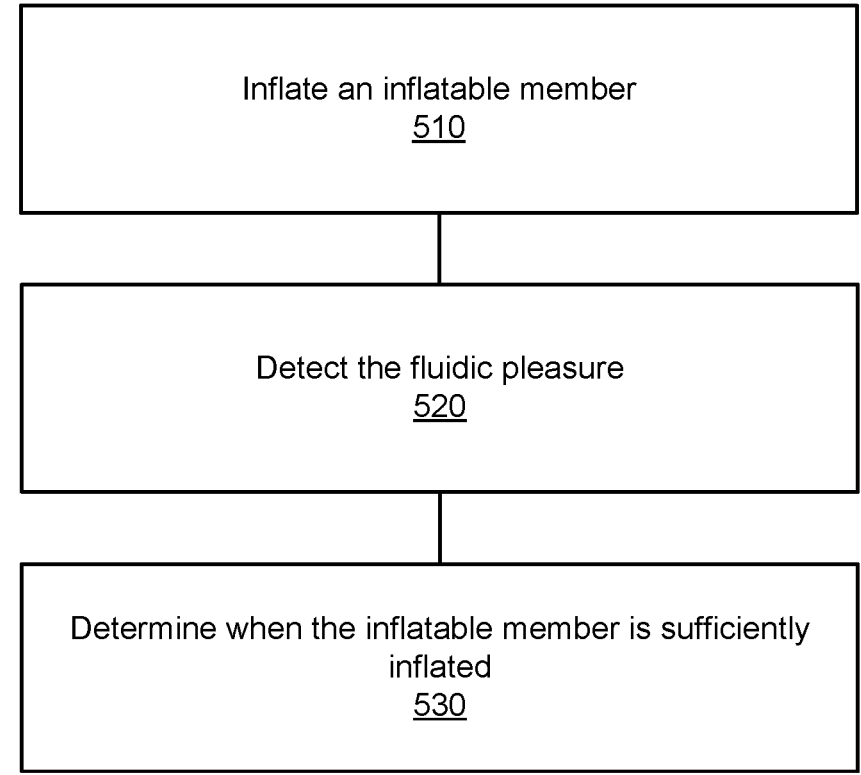

FIG. 7 is a flow chart of a method 500 according to an embodiment of the invention. In the illustrated embodiment, the method 500 includes at 510 inflating an inflatable member that is disposed within a body of the patient. In some embodiments, the inflatable member is configured to be disposed within a penis of a patient. At 520, the fluid pressure of the inflatable member is sensed or detected. At 530, it is determined when the inflatable member is fully inflated. For example, it can be determined when an inflatable member disposed within a patient is sufficiently expanded and/or sufficiently rigid.

Various implementations of the systems, modules, and other units described herein, and techniques described here can be realized in digital electronic circuitry, integrated circuitry, specially designed ASIC s (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. Various implementations of the systems and techniques described here can be realized as and/or generally be referred to herein as a circuit, a module, a block, or a system that can combine software and hardware aspects. For example, a module may include the functions/acts/computer program instructions executing on a processor (e.g., a processor formed on a silicon substrate, a GaAs substrate, and the like) or some other programmable data processing apparatus.

Some of the above example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium. A processor(s) may perform the necessary tasks.

Specific structural and functional details disclosed herein are merely representative for purposes of describing example embodiments. Example embodiments, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element and, similarly, a second element could be termed a first element, without departing from the scope of example embodiments. As used herein, the term and/or includes any and all combinations of one or more of the associated listed items.

The terminology used herein is for the purpose of describing particular embodiments only and is not intended to be limiting of example embodiments. As used herein, the singular forms "a", "an", and "the" are intended to include the plural forms as well, unless the context clearly indicates otherwise. It will be further understood that the terms comprises, comprising, includes and/or including, when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the above example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative embodiments, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as processing or computing or calculating or determining of displaying or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of non-transitory program storage medium or implemented over some type of transmission medium. The program storage medium may be magnetic (e.g., a floppy disk or a hard drive) or optical (e.g., a compact disk read only memory, or CD ROM), and may be read only or random access. Similarly, the transmission medium may be twisted wire pairs, coaxial cable, optical fiber, or some other suitable transmission medium known to the art. The example embodiments not limited by these aspects of any given implementation.

Detailed implementations are disclosed herein. However, it is understood that the disclosed implementations are merely examples, which may be embodied in various forms. Therefore, specific structural and functional details disclosed herein are not to be interpreted as limiting, but merely as a basis for the claims and as a representative basis for teaching one skilled in the art to employ the implementations in virtually any appropriately detailed structure. Further, the terms and phrases used herein are not intended to be limiting, but to provide an understandable description of the present disclosure.

While certain features of the described implementations have been illustrated as described herein, many modifications, substitutions, changes, and equivalents will now occur to those skilled in the art. It is, therefore, to be understood that the appended claims are intended to cover all such modifications and changes as fall within the scope of the embodiments.

What is claimed is:

1. An apparatus, comprising:
a bodily implant configured to be implanted into a body of a patient, the implant including an inflatable member, a sensor, and a calibration module,
the inflatable member being configured to be disposed within a portion of the body of the patient,
the sensor is operatively coupled to the inflatable member and is configured to detect a fluidic pressure within the inflatable member, and
the calibration module is configured to receive pressure data from the sensor and determine when the inflatable member is sufficiently inflated, the calibration module includes a smoothing module, the smoothing module being configured to smooth pressure data received from the sensor.

2. The apparatus of claim 1, wherein the inflatable member is configured to be disposed in an inflated configuration and a deflated configuration.

3. The apparatus of claim 1, wherein the inflatable member is configured to be disposed in an inflated configuration and a deflated configuration, the inflatable member being configured have a first rigidity when the inflatable member is in its inflated configuration and a second rigidity when the inflatable member is in its deflated configuration.

4. The apparatus of claim 1, wherein the inflatable member is configured to be disposed in an inflated configuration and a deflated configuration, the inflatable member being configured to have a first rigidity when the inflatable member is in its inflated configuration and a second rigidity when the inflatable member is in its deflated configuration, the first rigidity being greater than the second rigidity.

5. The apparatus of claim 1, wherein the bodily implant includes a pump, the pump being operatively coupled to the inflatable member and configured to pump a fluid out of the inflatable member.

6. The apparatus of claim 1, wherein the bodily implant includes a pump, the pump being operatively coupled to the inflatable member and configured to pump a fluid into the inflatable member.

7. The apparatus of claim 1, wherein the bodily implant includes a first pump and second pump.

8. The apparatus of claim 1, wherein the bodily implant includes an electric pump.

9. The apparatus of claim 1, wherein the bodily implant includes a first electric pump and a second electric pump.

10. The apparatus of claim 1, wherein the bodily implant includes a reservoir configured to hold fluid.

11. The apparatus of claim 1, wherein the calibration module includes an evaluation module, the evaluation module being configured to evaluate pressure data.

12. The apparatus of claim 1, wherein the inflatable member is configured to be disposed in a linear configuration and is configured be disposed within a penis of the patient.

13. The apparatus of claim 1, wherein the inflatable member is configured to be disposed within a penis of the patient.

14. The apparatus of claim 1, wherein the inflatable member is configured to be disposed in a linear configuration.

15. A method, comprising:
inflating an inflatable member that is disposed within a body of a patient;
sensing a pressure within the inflatable member;
smoothing pressure data received from a pressure sensor; and
determining when the inflatable member is sufficiently rigid.

16. An apparatus, comprising:
a bodily implant configured to be implanted into a body of a patient, the implant including an inflatable member, a reservoir, a first electrical pump, a sensor, and a calibration module,
the inflatable member being configured to be disposed within a portion of the body of the patient,
the first electrical pump being configured to pump fluid from the inflatable member to the reservoir,
the sensor is operatively coupled to the inflatable member and is configured to detect a fluidic pressure within the inflatable member, and
the calibration module is configured to receive pressure data from the sensor and determine when the inflatable member is sufficiently rigid, the calibration module includes a smoothing module, the smoothing module being configured to smooth pressure data received from the sensor.

17. The apparatus of claim 16, wherein the inflatable member is configured to be disposed within a penis of the patient.

18. The apparatus of claim 16, wherein the bodily implant includes a second electrical pump, the second electrical pump being configured to pump fluid from the reservoir to the inflatable member.

* * * * *